United States Patent
Ren

(10) Patent No.: US 8,068,919 B2
(45) Date of Patent: Nov. 29, 2011

(54) MICROWAVE HEATING APPARATUS AND METHOD FOR WHOLE-BODY OR REGIONAL HEATING

(75) Inventor: Changxue Ren, Changsha (CN)

(73) Assignee: Unimed Technologies, Inc., San Diego, CA (US)

( * ) Notice: Subject to any disclaimer, the term of this patent is extended or adjusted under 35 U.S.C. 154(b) by 1260 days.

(21) Appl. No.: 11/736,532

(22) Filed: Apr. 17, 2007

(65) Prior Publication Data

US 2007/0244530 A1    Oct. 18, 2007

(51) Int. Cl.
*A61F 7/00* (2006.01)
*A61B 18/18* (2006.01)
*A61B 18/00* (2006.01)

(52) U.S. Cl. ........ 607/101; 607/102; 607/154; 607/156; 606/33

(58) Field of Classification Search .................. 607/101, 607/102, 154, 156; 606/33
See application file for complete search history.

(56) References Cited

U.S. PATENT DOCUMENTS

| | | | |
|---|---|---|---|
| 4,586,516 A | 5/1986 | Turner | |
| 4,589,423 A | 5/1986 | Turner | |
| 4,632,128 A * | 12/1986 | Paglione et al. | 607/156 |
| 4,640,280 A * | 2/1987 | Sterzer | 607/154 |
| 4,669,475 A | 6/1987 | Turner | |
| 4,672,980 A | 6/1987 | Turner | |
| 4,798,215 A | 1/1989 | Turner | |
| 4,860,752 A | 8/1989 | Turner | |
| 4,974,587 A * | 12/1990 | Turner et al. | 607/101 |
| 5,571,154 A | 11/1996 | Ren | |
| 6,807,446 B2 * | 10/2004 | Fenn et al. | 607/101 |

* cited by examiner

*Primary Examiner* — Roy Gibson
*Assistant Examiner* — Kaitlyn Smith
(74) *Attorney, Agent, or Firm* — Morrison & Foerster LLP

(57) ABSTRACT

The invention provides a microwave heating method and apparatus for evenly heating an object, such as a person's body. The methods and apparatus involve use of microwave source (or sources) that outputs multiple microwaves that are non-correlated with each other in phase; an array of antennas that radiate substantially plane microwaves to form a pseudo uniform microwave electromagnetic field, where the microwaves are not phase-correlated, in order to eliminate non-uniform heating caused by interference. Each of the antenna array consists of multiple antenna units, each antenna unit consists of at least one microwave radiator and at least one converter that converts the spherical microwave to plane microwave. A computer based control system and a temperature monitoring subsystem can be used to adjust the output of each antenna, in order to enhance the uniform heating effect. The apparatus and method can be used to perform whole-body hyperthermia or regional hyperthermia.

21 Claims, 3 Drawing Sheets

MICROWAVE HEATING APPARATUS AND METHOD FOR WHOLE-BODY OR REGIONAL HEATING

TECHNICAL FIELD

The present invention relates generally to microwave heating, particularly to a microwave heating apparatus and method for using microwave to heat a large area of a lossy medium or a conducting medium by forming pseudo uniform microwave electromagnetic fields, which can be adjusted to provide even heating of a large mass that absorbs at least some of the microwave energy.

BACKGROUND ART

Microwave heating can be used to selectively deliver energy to certain types of molecules having dipole moments, such as water; the result of absorption of this energy is an increase in temperature, thus microwaves can be used to heat a portion of a lossy medium, such as the human body. It is also well known that a modest increase in temperature, such as heating to 42-44° C., can cause cancer cells to become much more susceptible to various methods of injuring or killing cells; thus increasing the temperature of a person's body during a cancer treatment can enhance the effectiveness of the treatment. One way to heat cancer cells in vivo is thus to apply microwave energy to the cells, which can be used for hyperthermia.

Since 1980, various hyperthermia methods have been developed to raise the temperature of part or all of the body of a cancer patient. These methods have been used locally (i.e., within a small area, such as directly in tumor tissue), regionally (in a larger portion of the body, such as a particular limb where a tumor is located), and even for the entire body of the patient (whole-body hyperthermia). Local and regional hyperthermia methods attempt to selectively warm a targeted tumor directly, without substantially affecting the rest of the patient's body. Whole-body hyperthermia is often used as a systemic treatment for a cancer condition that is delocalized or has metastasized. These methods have been shown to reduce some of the adverse effects caused by radiation and chemical cancer therapies, and to make these therapies more effective. Recent basic and clinical research shows that whole body hyperthermia may be widely applicable as an adjunct treatment used in combination with conventional chemotherapy and ration treatments, as methods for providing whole-body hyperthermia temperatures improve.

Heating methods used for hyperthermia treatments include exposure to warm air or water, as well as application of heat in the form of electromagnetic radiation, including infrared and microwave radiation. Microwave heating has been most effectively used for localized heating, where various means for focusing the microwave energy in and around the targeted tumor have been used. See, e.g., U.S. Pat. No. 5,571,154. Heated air or water tend to be too slow and uncomfortable for patients to endure. Most of the traditional whole-body hyperthermia devices use infrared (IR) heating technology. For example, ET-SPACE™, one of the whole-body heating apparatus manufactured by ET Medical Corporation of the P.R.China, is a hyperthermia apparatus using infrared radiation to heat a patient's body. This system raises body temperature by exposing the body to specific infrared frequencies. The infrared energy is absorbed at the surface of the skin, and the heated skin gradually transfers the heat to the fat and then to the muscle by conductive heat transfer. The heat is then slowly transferred to the inside of body where it warms the blood, which gradually increases the whole body temperature. Other devices known in the art utilize microwave energy to heat the body of a subject, but are generally designed to focus microwave energy in a local or regional treatment, e.g., U.S. Pat. Nos. 4,586,516; 4,589,423; 4,669,475; 4,672,980; and 4,798,215; and 4,860,752 appear to relate to localized treatment methods, and contemplate ways to utilize interference to focus energy selectively on a tumor to be treated.

However, there are several shortcoming with this type of device:

1. The infrared radiation cannot penetrate the skin, nor does it penetrate the fat or muscle. It relies on heat transfer from the skin, and the skin can only be heated modestly before pain and injury thresholds are exceeded.
2. The skin of a human body can incur severe skin burns when exposed to temperature higher than 46° C. for a long period of time, while muscle and other tissues will suffer if maintained at temperatures above about 43° C. Hence, the temperature inside an infrared treatment chamber can not be over about 45° C. for safety reasons. However, the normal human temperature is around 37° C. This means the temperature difference between the treatment chamber and human body is no more than about 8° C. As a result, heat transfer during such treatments is very slow, which results in long heating time—thus a single IR hyperthermia treatment usually last for 5-6 hours, because the body temperature increases very slowly toward the level where a significant hyperthermia effect occurs. Thus this method risks skin burn and other injuries, and stresses the entire body for a long period of time.
3. It is intolerable for a patient to stay inside an enclosed IR treatment chamber at 45° C. for 5-6 hours, so the patient must be put into deep anesthesia which adds additional stress and risk for the cancer patient, in addition to the stresses caused by the primary radiation or chemotherapeutic treatment that is being used.
4. The reported incidence of adverse effects from heating a subject with the ET-SPACE™ systems is 10.6%, consisting of 2nd degree skin burns and bedsores.
5. The infrared based device has limited application in that it cannot be used to perform regional hyperthermia. Thus a cancer treatment facility must have separate devices in order to provide local/regional hyperthermia treatments and whole-body hyperthermia treatments.

There is thus a need for improved methods and devices for heating a subject's whole body during hyperthermia treatments. Improved methods and devices should provide at least some of the following advantages: faster heating time, to achieve an effective body temperature more quickly; decreased risk of injuries caused by localized heating; reduced discomfort so that patients may not require prolonged or general anesthesia during hyperthermia treatment; and the flexibility to use a single device for both local/regional treatments and for whole-body hyperthermia treatments. The present invention provides devices and methods that offer such advantages.

Disclosure of the Invention

An object of the present invention is to overcome the shortcomings of the existing hyperthermia technology by providing a microwave heating apparatus and method that can produce a pseudo uniform microwave electromagnetic field that can be used to heat a targeted subject or other object. Microwave energy is used, because it is absorbed within the body, unlike infrared energy, which is absorbed almost entirely at the surface of the skin. A generally uniform field is used to deliver heating energy over a large area, permitting relatively rapid heating of a region or of the whole body. The microwaves in this generally uniform field penetrate through skin and fat, and can further penetrate 2-3 cm inside the muscle, hence their energy is absorbed within a relatively large volume of tissue, allowing delivery of a larger amount of energy than can be achieved by infrared technology, without excessive localized heating. Moreover, since heat is absorbed in a larger volume of tissue, it more quickly transfers heat into the blood to further accelerate distribution of the heat to portions of the body that do not receive substantial amounts of microwave energy. As a result, the time required to elevate the body temperature of a treated subject is greatly reduced, without localized heating of the skin that causes injury in an infrared heating device.

The pseudo uniform microwave electromagnetic field used in these devices and methods is formed using principles of non-interfering electromagnetic wave theory. The devices include one or more arrays of antenna units that are individually controllable, and that deliver substantially planar microwaves that are not phase correlated. Avoiding phase correlation eliminates constructive and destructive interference between waves from different antennas, which minimizes 'hotspots' and 'cold spots' that would develop where in-phase microwaves overlap. These substantially planar waves that are not correlated in phase are referred to as non-interfering microwaves.

The microwave frequency of the present invention can be any frequency between about 0.5 GHz and 10 GHz. In some embodiments, it can be in the range of about 2 GHz to about 3 GHz, such as about 2450 MHz.

The devices and method use a microwave source (or sources) that will ultimately provide non-interfering microwaves that are not phase correlated, where such non-interfering microwaves will be radiated by the antenna array. The microwave source (or sources) has a power output or multiple outputs that is/are suitable for generating non-interfering microwaves that are not phase correlated. A microwave source having only one output can be used by splitting the single output into multiple outputs with a splitter. Alternatively, multiple microwave generating sources may be used; and a combination of, e.g., two sources or three sources with one or more splitters may also be used to provide the desired number of separate microwaves to feed into an array of antennas. Once multiple microwaves are produced, the phase of the signals can be adjusted to avoid phase correlations between the microwaves before they reach the antennas of the antenna unit. This can be done by employing one or more random phase shifting devices, or a random phase generator, to adjust phasing of at least some of the microwaves before they reach the antenna units. In some embodiments of the invention, the phase of the microwaves from adjacent antenna units is not correlated; in others, each of the microwave antenna units provides a microwave output that is not phase correlated with any other antenna unit that operates at the same time.

The microwave source (or sources) with a power output or multiple outputs is suitable for heating a person's body rapidly enough to provide effective hyperthermia treatment. In whole-body treatment, the power may be divided among a number of different antenna units. Thus each antenna unit may radiate less power than is output by devices of the prior art; however, because there are many of the antenna units, the net result is efficient and rapid heating of the body without creating localized hotspots. In addition, because the power output by the individual units can be individually controlled, the user can electronically adjust the electromagnetic field so it is applied only by certain antenna units, which deliver microwave energy only to selected portions of the object. Thus the devices of the invention can also be used for regional hyperthermia treatments, directed to one portion of the body such as a limb.

In order to provide a pseudo uniform microwave field over a large area, the devices include antenna array or multiple arrays. Each antenna array consists of multiple antenna units. Each antenna unit comprises at least a microwave radiator that radiates a spherical wave, and at least a converter that converts the spherical microwaves to plane microwaves which are directed toward a targeted object. Thus each antenna unit provides a plane wave output, and the outputs of various units are non-interfering. The array of antenna units delivers plane waves over large portions of a targeted object such as a hyperthermia patient's body.

The antenna units are distributed relatively evenly around or at least on one side of a targeted subject or object, to deliver microwave energy onto and into the target to be heated. This reduces localized overheating and potential for injury. Because the antenna units produce plane wave outputs, the output power is mostly directed in an output column directly in front of the antenna unit. Properly spacing the antenna units apart reduces the overlap of the output columns of adjacent antennas. The antenna units in an array are generally separated by a distance that reduces overlap between the output columns of microwave output from other antenna units. This reduces interference between microwaves from different antennas, by minimizing the overlap between the microwave fields from different antenna units. Avoiding phase matching or phase correlation between at least adjacent antenna units further reduces such interference, to provide a uniform microwave field.

The power density and the distribution of the power density of the microwave electromagnetic field are adjustable, by a control system that controls the energy output of each antenna unit in the array. This results in quickly raising body temperature while the patient feels comfortable without deep anesthesia: it does not rely primarily on heating the subject's skin, which is rich in pain receptors and thus particularly heat sensitive. Furthermore, it greatly shortens the treatment time and it does not cause skin burns to the patient, thus it addresses many of the shortcomings of previous technology.

One aspect of the invention provides a microwave diathermy device for heating a lossy or conducting medium, said device comprising:
  a) at least one microwave source that provides microwaves through a multiplicity of microwave output ports, wherein each output port is operatively connected to send microwaves to an antenna unit; and
  b) a plurality of microwave radiating antenna units; wherein, each antenna unit comprises a radiator to produce a spherical microwave, and a converter to convert the spherical microwave into a substantially plane microwave,
  wherein the output microwave from each antenna unit is non-interfering with respect to the output microwaves from other antenna units.

The multiplicity of output ports may be on the microwave source, or they may be on a splitter or other device that receives microwaves from the microwave source and participates in delivery of the microwaves to one or more antenna units. Optionally, the device may also include a computer-based real-time control system and/or a temperature control sub-system, which may be linked together to allow the control system to adjust the output of the antennas to provide a desired heating rate, temperature, or temperature distribution within the heated object. The device may provide a pseudo uniform microwave field for heating the object. It may be configured to direct this microwave field onto at least one aspect, or at least a majority of one aspect of the object to be heated; and that object may be a human subject to be treated using hyperthermia.

Another aspect of the present invention provides a method of forming a pseudo uniform microwave electromagnetic field for heating an object. This method uses one or more microwave sources to produce multiple microwaves that are not correlated in phase. The multiple non-phase correlated microwaves are delivered to an array of antennas, or to multiple arrays of antennas, which are used to distribute the microwaves relatively uniformly over a target, such as a hyperthermia patient's body. The antennas radiate substantially plane waves, so they provide a more uniform microwave field than devices known in the art. Because an array of antennas is used, controlling the individual antennas permits the microwave energy to be selectively delivered to each region of the targeted object, thus enabling the user to achieve a desired temperature distribution within a relatively large object.

The device may provide microwaves within the range of about 0.5 to 10 GHz, preferably in the range of 2 GHz to 3 GHz, such as 2.45 GHz. It may utilize any suitable number and arrangement of antenna units to produce the microwave field, preferably by producing plane microwaves, and typically using at least four antenna units in an arrangement that may be sized suitably for producing a microwave field large enough to cover the majority of a hyperthermia subject's body. The plane microwaves may be produced as spherical microwaves by conventional antennas, and then converted by a converter into plane waves. Suitable converters may use a dielectric material having a refractive index greater than one; preferably the dielectric material has a refractive index of 1.2 to 1.3.

Each of the antennas in the array comprises at least one microwave radiator and at least one converter that converts a spherical microwave to a plane microwave. Hence, each antenna unit receives a microwave input from a microwave source, and the radiator of the antenna unit radiates a spherical microwave. The converter then converts this spherical wave to a substantially planar wave, which is directed toward the treated subject.

In addition, the device may include a temperature monitoring subsystem, such subsystem can use various temperature sensing technologies such as but not limited to thermistor, infrared sensor, MRI etc. to monitor temperature of the lossy object. At least one temperature sensor is placed either in contact with or not in contact with the medium to be heated by the array of antennas so that it measures a temperature of at least one portion of the medium to be heated. The temperature monitoring subsystem monitors heating to determine where a target temperature has been achieved, for example, and is operatively connected to a control system. The control system uses this temperature information from the temperature monitoring subsystem to adjust the power output of individual antennas in the antenna array. By adjusting the power density and the distribution of the power density of the planar microwaves from individual antenna units using electronic scanning, this method can be used in both whole body hyperthermia (including the body and limbs) and regional hyperthermia.

Another object of the present invention is to provide an apparatus that uses at least one array of antenna units to achieve a desired temperature distribution in a relatively large object, such as a person's body. The desired temperature distribution may be uniform throughout the targeted object, or it may include localized elevation of temperature of certain regions within the object. The apparatus includes one or more antenna arrays, consisting of multiple antenna units, and a microwave energy source that provides a multiplicity of microwave signals to power the antennas in the array. Each antenna unit comprises a microwave radiator that radiates a spherical wave, and a converter that converts the spherical microwave to plane microwaves which is used toward a targeted object. The microwave source typically includes more than one output port, or feeds into a splitter that divides the signal into more than one output. The microwave output is directed to the antenna units, which then output non-interfering microwaves, which are not correlated in phase. The apparatus may also include a computer based real-time control system and a temperature monitoring subsystem. The temperature monitoring subsystem can comprise one or more temperature measuring devices using various temperature measuring technologies that are adapted to measure a temperature of at least one portion of the targeted object.

Another aspect of the invention provides a method to establish a desired temperature distribution in an object by forming a pseudo uniform microwave electromagnetic field to heat at least a portion of the object, which method comprises:
  providing a microwave source that produces non-interfering microwaves that are not phase correlated; .
  providing at least one array of microwave antenna units, wherein each antenna unit receives microwaves from the microwave source and produces a substantially plane microwave, wherein the power output of each antenna unit can be adjusted by a computer based control system;
  providing a temperature monitoring sub-system adapted to measure the temperature of at least one portion of the object, wherein the temperature monitoring subsystem provides temperature information to the computer based control system;
  directing the substantially plane microwaves to form a pseudo uniform microwave electromagnetic field incident upon the object to be heated; and
  adjusting the power output of the antenna units in response to information from the temperature monitoring subsystem to achieve the desired temperature distribution in the targeted object.

The method may be used to produce a pseudo uniform microwave field sized to heat the entire body, or the majority of the body, of a subject to be treated with hyperthermia. Alternatively, it may be used to create a localized heating center in the body of a subject to be treated with hyperthermia.

Another aspect of the invention provides a method to use microwave energy to elevate the temperature of a subject's body, characterized by use of substantially planar microwaves delivered by an array of antenna units that direct the microwaves onto a majority of one aspect of the subject's body, wherein the microwaves are not correlated in phase. The method can further incorporate using a temperature monitoring subsystem, such as a multiplicity of temperature sensors. The temperature monitoring subsystem typically measures a temperature at one or preferably more than one location in or on the object to be heated. The method can also incorporate using a control system such as a computer-based real-time control system that uses the temperature measurements to adjust the power output of some of the antenna array, or of some or all of the antenna units in the array, to achieve the desired temperature distribution in the heated object. In some embodiments, the method is used to provide a hyperthermia treatment to a subject in need of such treatment.

Frequently, the temperature monitoring subsystem in such embodiments includes multiple temperature sensors in contact with or not in contact with the subject, but measuring a temperature of a portion of the subject's body. These temperature measurements are delivered to a control system, which uses this information to adjust the power output of one or more antenna units to facilitate producing a desired temperature distribution or rate of temperature change in the treated subject. These methods are frequently used to treat a subject having widespread, or metastasized or delocalized cancer, and are often employed in combination with a radiation or chemotherapy treatment method, and to enhance the effectiveness of the radiation or chemotherapy treatment.

The control system can be used to provide electronic scanning, which refers to using the temperature monitoring subsystem to measure the temperature of a subject's body at one or more positions on or in the body, and feeding those temperature measurements to the control system, which uses the temperature information to adjust the power output of the individual antenna units in the antenna array. By controlling power output by the microwave source(s) and by the individual antenna units, the control system ensures that the targeted subject's body is heated to a sufficient temperature without injury.

The output of a non-interfering microwave source is connected to each antenna unit; the radiator in the antenna unit produces a spherical microwave and the converter converts the microwave into a plane wave, that impinges on the targeted object. The array comprises multiple antenna units that may be held in position by a frame, and may be of any shape or arrangement suitable for a particular use. FIG. 2 provides an illustration of one embodiment of a frame carrying an array of antenna units.

The devices and methods of the invention thus provide an array of antenna units that receive microwaves from one or more microwave sources. The antenna units convert these signals into plane wave microwaves that are incident on the targeted subject. The plane waves are not phase correlated, so they do not produce substantial constructive interference that would cause localized heating. Thus a pseudo uniform microwave field can be generated. In use, the device may include a temperature monitoring subsystem and a control system, wherein the control system uses temperature information from the temperature monitoring subsystem to adjust the output power of each antenna unit as needed to heat the whole body or a region of the body as needed. The energy delivered into the body is redistributed by blood circulation to facilitate rapid heating for whole-body hyperthermia treatments. Electronic scanning can be used to adjust the power output and distribution based on input from the temperature monitoring subsystem, and can also be used to provide localized heating for a regional hyperthermia treatment, e.g., by selectively heating an area, region or limb, such as one where a tumor is located. In addition, unlike an infrared treatment method, the invention can be used without enclosing the subject in a chamber, so it is easier to permit air circulation to cool the subject's skin, further reducing the risk of injury and promoting the comfort and safety of the treated subject, who would not require prolonged or deep anesthesia during treatment.

In another aspect, the invention provides a microwave diathermy device for heating a lossy or conducting medium, which device comprises:
 a) an array of antennas, and
 b) means to generate a plurality of microwaves that are not correlated in phase;
 wherein each of the plurality of microwaves is directed to at least one of the antennas. The means for generating a plurality of microwaves may be a single microwave generating source whose output is then split by a splitter into a multiplicity of separated microwaves that are directed to individual antenna units in the antenna array; wherein at least some of the separated microwaves are phase adjusted by a phase shifter before the signals reach the antennas, so that the microwaves output by the antennas are not correlated in phase. In other embodiments, the means for generating a plurality of microwaves comprises two or more microwave sources that generate microwaves that are not phase correlated; the outputs of these microwave sources may be further split as needed to provide a suitable number of microwaves to feed each antenna unit in the array so that the outputs from the antenna units are non-interfering microwaves. In many embodiments, the antenna arrays receive microwave from the microwave source(s) and outputs spherical microwaves, which the antenna units then convert into plane waves that are incident upon the object to be heated.

MODES OF CARRYING OUT THE INVENTION

Figure 1:
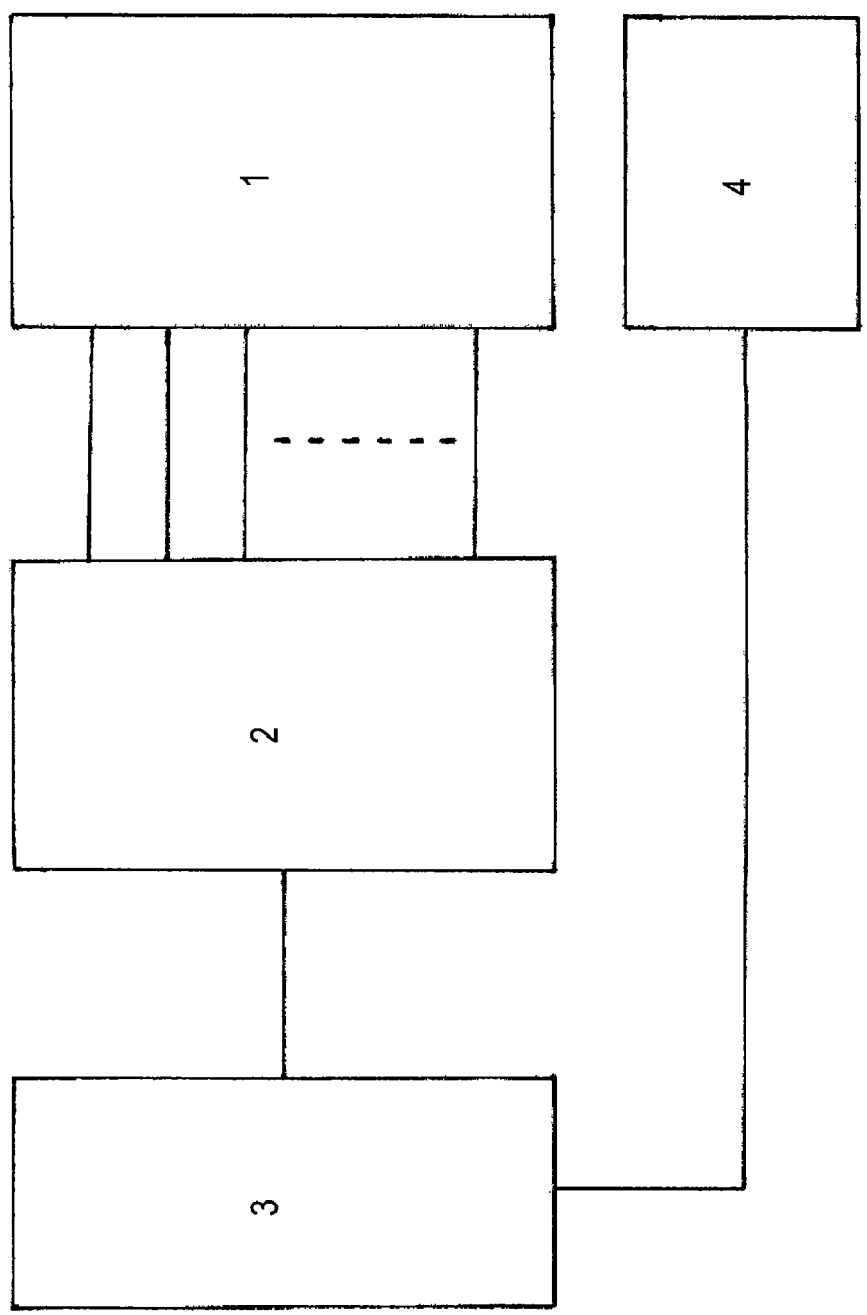
FIG. 1 is a block diagram illustrating the microwave heating apparatus of the present invention;
 (1) antenna array,
 (2) non-interference microwave source,
 (3) computer based real time control subsystem, and
 (4) temperature monitoring subsystem.

The devices and methods of the invention use pseudo uniform microwave field to heat an object or medium, which may be a lossy medium or a conducting medium. An example of a lossy medium is one having a substantial water content, since water absorbs microwave radiation relatively well. Notably, however, microwave radiation can penetrate into a water-containing object by at least a few centimeters, allowing the microwave energy to be absorbed within the object, while shorter and longer wavelengths would be either absorbed entirely at the surface of the object or transmitted through the object without efficient absorption.

The term "whole-body" as used herein means heating the human body, including the limbs to a temperature above its normal homeostatic temperature. Because heat is redistributed by conduction and by the circulating blood, whole body hyperthermia can be achieved without covering every square inch of the subject's body with microwave radiation, but it typically involves administering microwave heating to at least a majority of one aspect of the subject's body.

'One aspect' of the body as used herein refers to, for example, the front or back of the body, or one side of the body. The methods and devices described herein operate successfully by delivering microwaves to one aspect or to more than one aspect of the body; thus, for example, an array of microwave antennas in a substantially flat frame could be positioned above a person's prostrate body, and would deliver microwaves to the front of the body only. This is quite sufficient to heat the entire body of the subject, because other mechanisms redistribute the heat energy as it builds up in the areas where microwaves are absorbed. Alternatively, an array of antennas could be curved or contoured to partially surround a person's body, and could, for example, deliver microwaves to the front and sides of a person's prostrate body. In other embodiments, the person could be standing upright or could be seated, and one or more antenna array could surround most of the person's body.

The term "control system" refers to a computer based real time control system. It can consists of one or more computers (for example, the computer may be one or more microprocessors or microcontrollers, or it may be a computer network, personal computer, etc.), one or more display devices or terminals, user input devices such as key board, mouse, or touch screen; and computer peripherals for control and sampling purpose. The computer based control sub-system can also have the networking connection to access local area network or wide area network for remote access. The computer based real-time control sub-system takes the user inputs from the input device, sets the selected operating mode. According to selected operating mode, it can run through an algorithms and produce one or more antenna control signals to modulate the output of one or more antenna units or of the non-interfering microwave source(s). Thus it controls and adjusts the output power of the non-interfering microwave source and/or the output of individual antennas and consequently changes the distribution of the power density of the electromagnetic field and hence adjusts the temperature of the diathermized position in the medium inside the electromagnetic field.

The term "electronic scan" as used herein refers to the following process: using a temperature monitoring sub-system having one or more temperature sensors either in contact or non-contact with the object to be heated, to measure the temperatures at different parts of the object such as a human body; sending temperature information from the sensors of the temperature monitoring subsystem to a control system, such as a computer based real-time control system; and having the control system use the temperature information to modify the microwave energy being delivered to the object by the array of plane-wave radiators. The control system processes the temperature information it receives to determine what the temperature distribution inside the targeted object appears to be, and compares that to a desired temperature distribution. For example, in a whole-body hyperthermia treatment, the control system could be programmed to achieve a particular uniform target temperature, such as 43° C., throughout the targeted object. The control system would then calculate a control signal for one or more of the antenna units in the antenna array, which often controls each antenna unit separately. The control signal would adjust the power density and/or the distribution of the power density produced by the antenna array, in order to increases the rate of heating in 'cool' spots in the targeted object and it could stop heating areas that have achieved or exceeded their target temperature by turning the power down or off for antennas that most directly deliver microwaves to those areas.

The devices and methods use at least one microwave source to power an array of antenna units. One microwave source is sufficient, provided it has multiple output ports or its output can be split to provide multiple output ports, so that there are enough outputs to feed a microwave to each antenna unit. However, multiple microwave sources can be used, and can be adapted or controlled to provide non-interfering microwaves. The microwaves that are output from one or more microwave sources can be modified to be non-interfering at any point prior to their emission from the antenna unit as non-interfering plane waves.

Figure 2:
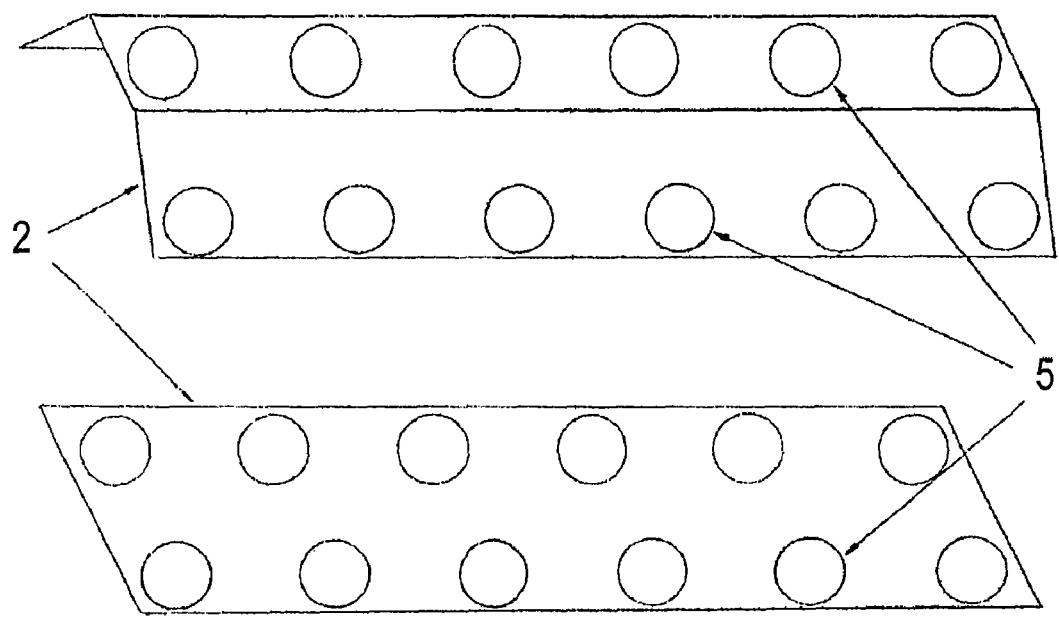
FIG. 2 is a depiction of a preferred embodiment of the antenna array in the microwave heating apparatus of the present invention.
Figure 3:
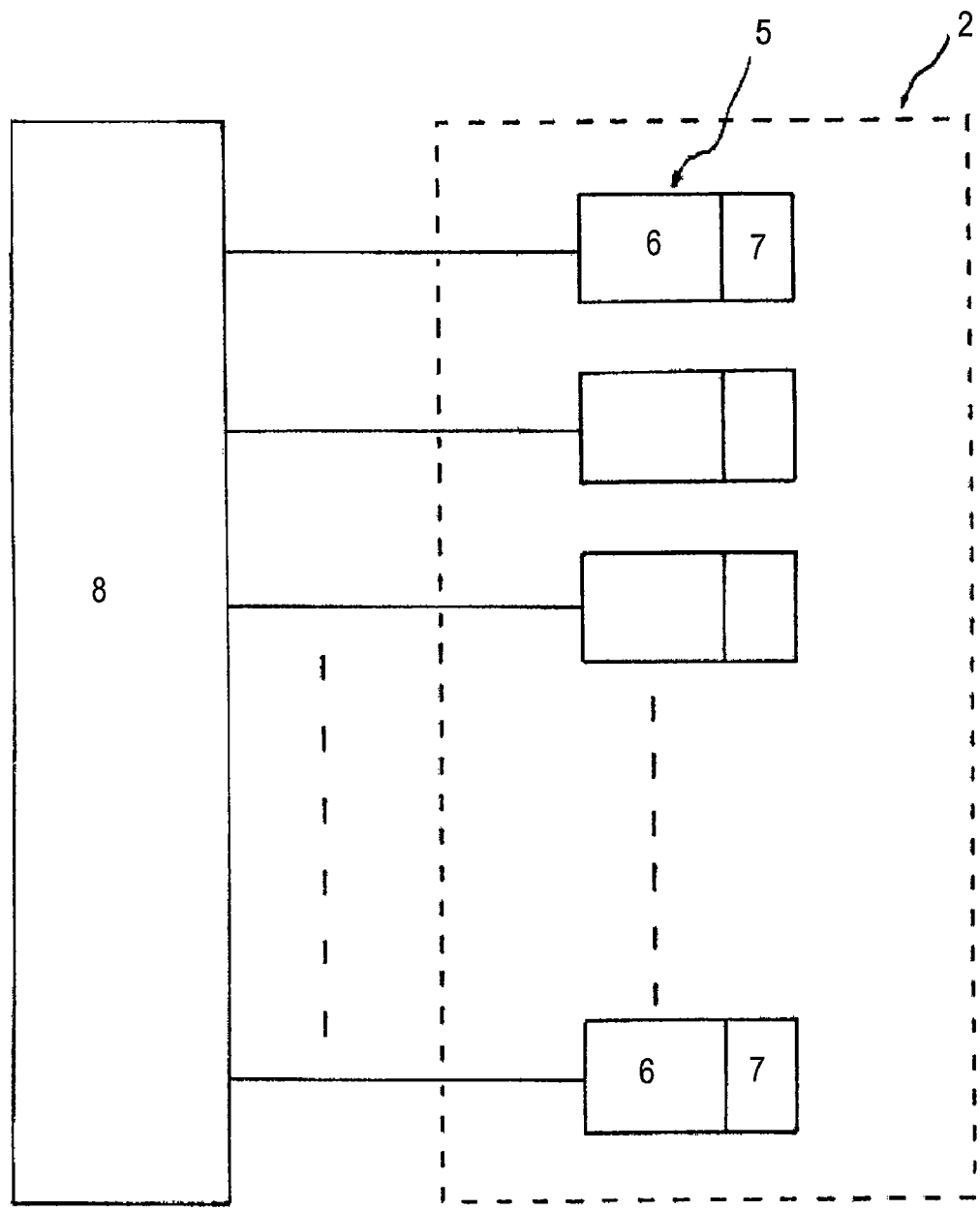
FIG. 3 is a block diagram of an embodiment of the device, illustrating the following features:
 (a) antenna array (2)
 (b) non-interference microwave source (8),
 (e) antenna units (5)
 (f) microwave radiator (6)
 (g) converter (7) that converts the spherical microwave to plane microwave.

The array of antenna units can be of any shape or arrangement to fit different needs. For example, a relatively flat frame may be used to support and position the antenna units. A frame that is contoured to wrap partially around a person's body can be used for a device specifically adapted for whole-body hyperthermia. In some embodiments, the frame is flexible and permits the user to adjust to some degree the shape of the array of antennas so that it fits each object or each patient. Illustrative examples are shown in FIG. 2.

The size of the array can be any that is suitable for the particular application, and is determined partly by the size and spacing of the antenna units. In some embodiments, the array is at least about three square feet in area, so it can be used to apply plane microwaves to an object of about that size. In other embodiments, the array is at least about five square feet in area. In some embodiments, the antenna array is at least about four feet in its longest dimension so it can be used to apply microwave energy over the majority of the body of an adult person. The array comprises a plurality of antenna units, and can include four or more antenna units, or ten or more antenna units. In some embodiments, it includes 8 or more, and optionally 16-32 or more antenna units. The antenna units may be 5-10 or 10-15 or 15-20 cm in their major dimensions, or they may be larger or smaller when consistent with their function. They may be symmetric, e.g. square, rectangular or circular in shape, or they may be irregular in shape. They may be placed close together (e.g., each may be less than 2 cm from its nearest neighbor), or they may be spaced further apart. In some embodiments, their spacing is described according to the distance between the center point of the face of each antenna unit, and that spacing may be about 5 cm or about 10 cm or about 15 cm or about 20 cm, or it may be 25 cm or more.

The principle method of the present invention includes use of an antenna array to transform multiple microwaves into approximate plane waves, to form a pseudo uniform electromagnetic field which surround and impinge upon a human body. The plane microwaves are directed toward and incident upon at least one aspect of a person's body to induce hyperthermia. The microwaves can penetrate through skin and fat, and further penetrate 2-3 cm into the muscle tissue, to directly heat the muscle and blood. Because the multiple non-interfering microwaves are not correlated in phase, they will not cause interference with each other after radiating from the antenna units; the superimposed microwaves thus form a pseudo uniform electromagnetic field incident upon and/or surrounding the human body when all of the units are operating, so no over-heated spot will be produced during the initial phase of heating, yet the thermal energy can penetrate deeply into the human body, greatly reducing the time to raise a patient's body temperature to the target temperature required by the treatment. The patient's circulating blood helps transfer heat to the whole-body to ensure the subject's temperature rises rapidly throughout the whole body.

Another method of the present invention is to use electronic scanning to operate outside of the pseudo uniform field method. While the device can achieve substantially uniform energy delivery over the entire body of a subject, in many applications that is not all that is required. For example, when heating a person's body, microwave energy will be absorbed with different efficiencies in different portions of the body, and the heat produced will be redistributed at different rates in different tissues. Thus even though the energy field applied is uniform, the resulting changes in temperature in the subject's body will not be. Rather, some areas will heat more quickly and others more slowly. Accordingly, the device and methods of the invention provide a control system that can individually control each antenna in the array, preferably using a continuously variable power control mechanism. The control system can adjust the power density and power distribution from each antenna unit to provide even heating throughout the body if desired, or it can be programmed to form a heating center. The heating center is usually the place where a tumor is located, and the device can be used to produce higher temperature inside the tumor than in the surrounding regions by adjusting the power of the antenna units to maximize delivery of microwave energy to the affected tissue or region. Such method can be used to perform deep local or regional hyperthermia, using the same device that is also well suited to provide whole-body hyperthermia treatment.

The pseudo uniform electromagnetic field of the invention is not perfectly uniform, due to practical limitations; however, the use of plane waves provides much more uniform heating than devices using a spherical microwave source or sources. Thus some aspects of the invention employ a generally planar microwave, which is known in the art as distinct in characteristics from a 'spherical' wave, eve if it is not entirely planar. This plane waves provide a more even thermal energy delivery method than a device using a spherical microwave, because spherical microwaves deliver most of their energy into a relatively small area, creating local 'hot spots' in the targeted object. Even the use of multiple spherical wave sources produces localized 'hot spots' in the region nearest each radiator. An array of planar wave radiators, by comparison, provides a more nearly uniform energy distribution over a relatively large surface, such as a human body. The devices and methods of the invention employ an array of antennas to create a 'patchwork' of plane microwaves that can, in certain embodiments, effectively cover at least the majority of one aspect of a targeted object, such as one aspect of a human body.

The pseudo uniform electromagnetic field produced by the array of antennas is distributed in a relatively large volume that includes at least part of a targeted object. The power density of such field in a unit area is much smaller than that produced by a single antenna would be, assuming both are using the same amount of total power to perform hyperthermia. However, because it delivers energy over a larger area, and indeed a larger volume, of the targeted object, it can introduce more thermal energy overall than a single higher-powered antenna, and it can do so without focusing that energy into a small volume, which would cause injury to a human subject, for example. Plus, no enclosed treatment chamber is needed using the present invention, since heat is delivered into the subject rather than just onto the surface of the subject; this allows the air at about normal ambient temperature, or even cooled air, to naturally cool down the patient's skin. This improves patient comfort in hyperthermia treatments, because the skin is where the greatest perception of pain may occur, and where the patient's body has fewer methods for reducing the build-up of heat, i.e., while internal tissue has greater blood flow and is surrounded by other water-laden material that can help redistribute heat that begins to build up, the skin has only air on one side and has a relatively low blood flow, and at the same time it has many pain sensors; thus avoiding heat build-up at the skin is a critical factor in avoiding discomfort and injury. As a result of the relatively even heat distribution and the delivery of energy into the tissue rather than just onto the surface of the skin as an IR heater would do, the patient using the present invention's methods and devices feels comfortable and does not need to be deeply sedated. More importantly, the methods and devices described herein greatly reduce the risks involved with longer heating time required by IR technologies, and they do not burn the skin of the patient as IR devices can, thus the invention overcomes many of the shortcomings of previous technology.

In one aspect, the invention provides a microwave diathermy device for heating a human subject's body, which device comprises:
  at least one microwave source;
  a multiplicity of microwave output ports, wherein each output port is operatively connected to receive microwaves from a microwave source and to output microwaves to an antenna unit;
  a plurality of microwave radiating antenna units;
    wherein each antenna unit is operatively connected to receive microwaves from one of said output ports, and each antenna unit comprises a radiator to produce a spherical microwave, and a converter to convert the spherical microwave into a plane wave;
  wherein the output of each antenna unit is non-interfering with respect to the output of other antenna units.

Optionally, the device further comprises a temperature monitoring subsystem and a control system that receives input from the temperature monitoring subsystem, wherein the control system is adapted to adjust the power output of one or more of the antenna units in response to input from the temperature monitoring subsystem.

Typically, the antenna units are oriented to direct the pseudo planar microwaves they produce toward a surface of a targeted object to be heated, e.g., toward one aspect of the body of a subject to be treated via hyperthermia.

The devices may thus be sized to provide a substantially uniform field of plane microwaves over the majority of one aspect of a human subject's body. For example, it may be sized to produce a pseudo uniform microwave field over an area of about three square feet. It may also be sized so that its longest dimension is at least three feet long, or at least four feet long. Alternatively, the devices can be sized to perform localized hyperthermia using the method in this invention, so it can be sized to much smaller dimensions.

The devices of the invention may have an adjustable or continuously adjustable output power and operate at a single operating frequency or multiple operating frequencies, such as at least one frequency between about 0.5 GHz and 10 GHz. In some embodiments, the apparatus includes at least one microwave source that provides microwaves in the 2000 MHz to 3000 MHz frequency range. Optionally, more than one microwave source can be used. In a preferred embodiment, at least one microwave source provides microwaves at a frequency of about 2450 MHz.

The antenna unit includes a radiator that produces a spherical wave, and a converter to convert this spherical wave into a plane wave. In some embodiments, the converter operates by refractive principles, and uses a refractive element that comprises a dielectric material with a refractive index of 1.2 to 1.3, such as 1.23.

In certain embodiments, the array of antenna units comprises at least four antenna units, and the control system is adapted to individually control the output power of each antenna unit. In some such embodiments, the device further comprises one or more temperature sensors adapted to be either in contact or non-contact with the targeted object while the device is in use.

The invention also provides hyperthermia treatment methods, such as a method to establish a desired temperature distribution in a targeted lossy or conducting object by heating at least a portion of the object, which method comprises:

providing a microwave source (or sources) that is adapted to deliver microwaves to an array of antenna units, providing an array or multiple arrays of microwave antenna units, wherein each antenna unit produces a substantially plane microwave and the power output of each antenna unit can be adjusted by a control system;

wherein the substantially planar microwaves radiated by the individual antenna units are not phase correlated with overlapping microwaves radiated by other antenna units;

providing a plurality of temperature sensors, wherein each temperature sensor communicates to the control system the temperature at a region within the targeted object;

applying plane microwaves to the targeted object using the array of microwave antenna units, wherein the plane microwaves are phased to be non-interfering; thus forming a pseudo uniform microwave electromagnetic field around the heated object; and adjusting the power output of the antenna units in response to information from the temperature sensors to achieve the desired temperature distribution in the targeted lossy object.

In another aspect, the invention provides a method to use microwave energy to elevate the temperature of a subject's body for a hyperthermia treatment, where the method is characterized by use of substantially plane microwaves delivered by an array of antenna units that direct the microwaves onto a majority of one aspect of the subject's body, wherein the microwaves are not correlated in phase where they overlap. In these methods, a plurality of temperature sensors can be used to measure the temperature of the subject's body at different points, and the temperature measurements may be used to adjust the power output of antenna units in the array of antenna units in order to produce a desired temperature distribution within the subject's body.

The methods of the invention are sometimes used for treating a subject with a cancer that is widespread or delocalized, or one that has metastasized. This treatment includes elevating the temperature of the subject's body to increase the effectiveness of a cancer treatment such as chemotherapy or radiation therapy.

The following examples are illustrative of some preferred embodiments only, and are not intended to limit the scope of the invention.

EXAMPLE 1

In one embodiment of the microwave heating method for whole-body or regional heating, the invention uses non-interfering microwave sources to output 32 microwaves that are not correlated in phases; then it sends the 32 microwaves to corresponding antenna units in the antenna array to form a pseudo uniform microwave electromagnetic field. A patient is introduced into this field, which surrounds and penetrates the patient's body to elevate the patient's body temperature for a hyperthermia treatment. Each of the antennas is positioned to deliver energy to a particular region of the patient's body, so that the majority of the patient's body is covered by one of the antennas, and there is minimal overlap of the surfaces covered by the individual antenna units in the array of antennas. While the electromagnetic radiation heats the patient's body, electronic scanning technology is used to adjust both the power density and the distribution of the power in the electromagnetic field by turning each of the antenna units up, down, or off, as required.

Determining which antenna units to turn up or down is done by a control system. The control system collects temperature information from one or more locations in or on the treated subject, and compares it to a desired temperature or temperature distribution set by the user, such as a uniform temperature target of 43° C., or a similar suitable hyperthermia temperature level. The temperature information about the treated subject may be collected by any conventional means, but in a preferred embodiment, that information is collected by a plurality of temperature sensors on or in the subject's body. In this example, the device includes 32 temperature sensors, one of which is positioned in the region of the patient's body that is directly irradiated by each of the 32 antennas, so each antenna is associated with a particular temperature sensor. The control system then correlates the temperature information from the sensors to determine whether each antenna needs to have its power turned up or down.

This electronic scanning continues until the desired temperature distribution within the patient's body is achieved. The controlled microwave heat delivery is then continued for the desired therapeutic time period, which can be selected by a user of the device. Selection of the temperature target and the time duration of the treatment are well within the art, based on extensive literature regarding hyperthermia treatments, and depend upon the age and condition of the patient and on what type of therapy (e.g., chemotherapy or radiation therapy) the hyperthermia treatment is being used to enhance.

EXAMPLE 2

An exemplary device of the invention is depicted schematically in the Figures. As shown in FIG. 1, the apparatus consists of an antenna array (1), at least one source of non-interfering microwaves (2), a computer based real-time control system (3) and a temperature monitoring subsystem (4), preferably including a plurality of temperature sensors that are suitable for use within the heated zone of the targeted object. The antenna array (1) is mounted in a frame as shown in FIG. 2 and consists of, for example, 16 antenna units (5), each antenna unit comprising a microwave radiator (6) and a converter (7) that converts the spherical microwave to a plane microwave. The microwave source (2) has, e.g., 16 output ports that output 16 microwaves which are non-correlated in phase. In some embodiments, phase correlation is avoided by applying a random phase adjustment to one or more of the microwaves before it reaches the radiating antenna. The microwave source (2) has a continuously adjustable output power range of 0-3 kW and an output frequency in the range of 0.5-10 GHz. Preferably, the frequency is adjustable by the user. In one embodiment, the frequency is between 2 and 3 GHz, and can be 2.45 GHz.

Each output port of or connected to the non-interfering microwave source is connected to an input for a corresponding microwave antenna unit in the antenna array; each antenna unit includes a radiator and a converter. The radiator produces a spherical microwave, which then passes through the converter. The converter transforms the spherical microwave into a plane microwave. The converter in the antenna unit is made using a functional material that is synthetic and is a dielectric material with a refractive index of 1.23 (the refractive index of the functional material of the converter is >1, and the optimal value of the refraction index of the converter is within the range of 1.2-1.3). Methods for making suitable converters are known in the art.

The computer based real time control system adjusts both the output power of the microwave source and the distribution of power density of the microwave field based on the inputs it receives from the temperature monitoring subsystem. Electronic scanning can be used to perform whole-body heating, and it can be used to provide a non-uniform output when the temperature distribution indicates that non-uniform heating is needed to achieve the desired temperature distribution in the targeted object. The control system can be programmed to adjust the output of each antenna unit in the array to achieve the desired temperature distribution within the targeted object, which can be a uniform temperature for whole-body hyperthermia, or it can be non-uniform, in which case the control system can be programmed to adjust the power density and power distribution to form a heating center—for deep regional or local hyperthermia. In an exemplary embodiment, the temperature monitoring subsystem (4) has 6 sensors that are accurate to within ±0.1° C.

When the microwave heating apparatus and method of the present invention are used to treat a cancer patient, the patient will only feel warm in the irradiated parts of the body, without experiencing hot-spots that would cause injury, and minimal uncomfortable sensations or side effects will be experienced. The microwave heating apparatus using a pseudo uniform electromagnetic field and electronic scanning based on multiple temperature sensors in or on a patient's body is safe, reliable, and easy to operate.

Although the present invention has been explained above by way of a preferred embodiment thereof, it should be pointed out that any modifications apparent to the skilled user are included in the invention, and these preferred embodiments do not limit the scope of the invention.

The invention claimed is:

1. A microwave diathermy device for heating a lossy or conducting medium, said device comprising:
   a) at least one microwave source that provides microwaves through a multiplicity of microwave output ports; and
   b) a plurality of microwave radiating antenna units; wherein each antenna unit comprises a radiator to produce a spherical microwave and a converter to convert the spherical microwave into a substantially plane microwave, wherein the output microwave from each antenna unit is non-interfering with respect to the microwaves from other antenna units, and wherein each output port of the at least one microwave source is operatively connected to output microwaves to one of the plurality of microwave radiating antenna units.

2. The device of claim 1, which further comprises a temperature monitoring subsystem and a computer based control system that receives input from the temperature monitoring subsystem,
   wherein the computer based control system is adapted to adjust the power output of one or more of the antenna units in response to input from the temperature monitoring subsystem; and
      wherein the temperature monitoring subsystem is adapted to measure a temperature of at least one portion of the medium while the device is in use.

3. The device of claim 1, wherein the microwave source produces multiple non-interfering microwaves that are not correlated in phases; or the microwave source produces a single microwave that is split into multiple output microwaves, and the output microwaves are thereby converted into non-interfering microwaves that are not correlated in phases before they are radiated from the antenna units.

4. The device of claim 1, wherein the antenna units are oriented to direct the substantially plane microwaves toward a surface of a targeted object to be heated; wherein the antenna array is configured to provide a pseudo uniform field of microwaves over the majority of one aspect of a lossy medium to be heated.

5. The device of claim 1, wherein the microwave source has a continuously adjustable output power and operates in a frequency between about 0.5 GHz and 10 GHz.

6. The device of claim 1, wherein the microwave source produces microwaves having a frequency between 2 GHz and 3 GHz.

7. The device of claim 1, wherein the functional element of the converter comprises a natural or synthetic dielectric material with a refractive index greater than 1 ($n_D > 1$).

8. The device of claim 7, wherein the refractive index is between 1.2 and 1.3.

9. The device of claim 1, wherein the array of antenna units is capable of producing a pseudo uniform microwave field that is sized to be used for whole-body hyperthermia.

10. The device of claim 9, wherein the array of antenna units comprises at least four antenna units, and the computer base control system is adapted to control the output power of each antenna unit.

11. The device of claim 10, which further comprises a temperature monitoring sub-system that provides a temperature sensor associated with each antenna unit, and a computer-based controller that is adapted to adjust the output of each antenna unit to achieve a desired temperature at its associated temperature sensor.

12. The device of claim 1, wherein the substantially planar microwaves have a frequency in the range of about 0.5 GHz to about 10 GHz.

13. A microwave diathermy device for heating a lossy medium, said device comprising:
   a) an array of antennas, and
   b) means to generate a plurality of microwaves that are not correlated in phase;
   wherein each of the plurality of microwaves is directed to at least one of the antennas, wherein a spherical microwave output from each of the antennas is converted by a converter into a substantially plane microwave, and wherein the conversion occurs after the microwave is output from each of the antennas.

14. The device of claim 13, wherein the means to generate a plurality of microwaves comprises two or more microwave sources that are adapted to produce microwaves that are not correlated in phase.

15. The device of claim 13, wherein the means to generate a plurality of microwaves comprises a microwave energy source, a splitter to divide the output of the microwave energy source into a multiplicity of separated microwaves, and a phase shifter adapted to shift the phases of the separated microwaves fed into a plurality of microwave antennas, whereby the antennas produce microwave outputs that are non-interfering.

16. The device of claim 15, wherein the phase shifter is a random phase shifter adapted to randomly shift the phases of the separated microwaves.

17. The device of claim 13, wherein the array of antennas is adapted to prevent interference between the microwave outputs.

18. The device of claim 17, wherein the array generates a pseudo uniform microwave electromagnetic field.

19. The device of claim 13, wherein the substantially plane microwaves have a frequency in the range of about 0.5 GHz to about 10 GHz.

20. The device of claim 13, wherein a functional element of the converter comprises a natural or synthetic dielectric material with a refractive index greater than 1 ($n_D > 1$).

21. The device of claim 20, wherein the refractive index is between 1.2 and 1.3.

* * * * *